(12) United States Patent
Becking

(10) Patent No.: US 9,039,726 B2
(45) Date of Patent: May 26, 2015

(54) FILAMENTARY DEVICES FOR TREATMENT OF VASCULAR DEFECTS

(75) Inventor: Frank P. Becking, Palo Alto, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/911,034

(22) Filed: Oct. 25, 2010

(65) Prior Publication Data

US 2011/0208227 A1  Aug. 25, 2011

Related U.S. Application Data

(63) Continuation of application No. 12/427,620, filed on Apr. 21, 2009, now Pat. No. 8,142,456.

(60) Provisional application No. 61/046,594, filed on Apr. 21, 2008, provisional application No. 61/046,670, filed on Apr. 21, 2008, provisional application No. 61/083,957, filed on Jul. 28, 2008, provisional application No. 61/083,961, filed on Jul. 28, 2008, provisional application No. 61/145,097, filed on Jan. 15, 2009.

(51) Int. Cl.
*A61M 29/00* (2006.01)
*A61B 17/12* (2006.01)
*A61M 29/02* (2006.01)
*A61B 17/00* (2006.01)
*A61B 18/00* (2006.01)

(52) U.S. Cl.
CPC ...... *A61B 17/12022* (2013.01); *A61B 17/12109* (2013.01); *A61B 17/12113* (2013.01); *A61B 17/12118* (2013.01); *A61B 17/1215* (2013.01); *A61B 17/12172* (2013.01); *A61M 29/02* (2013.01); *A61B 2017/00526* (2013.01); *A61B 2017/00867* (2013.01); *A61B 2018/00416* (2013.01); *A61B 2017/12054* (2013.01); *A61B 2017/12068* (2013.01); *A61B 2017/1205* (2013.01)

(58) Field of Classification Search
USPC ................ 606/159, 191, 200, 113, 114, 127; 604/105; D24/143
See application file for complete search history.

(56) References Cited

U.S. PATENT DOCUMENTS 4,425,908 A   1/1984  Simon
4,619,246 A  10/1986  Molgaard-Nielsen et al.
(Continued)

FOREIGN PATENT DOCUMENTS

CA       2607529       4/2008
CN    101472537 A      7/2009
(Continued)

OTHER PUBLICATIONS

PCT/US2009/041313 Partial International Search Report, Sep. 30, 2009.
(Continued)

*Primary Examiner* — Victor Nguyen
*Assistant Examiner* — Kevin Everage
(74) *Attorney, Agent, or Firm* — Elizabeth A. O'Brien, Esq.

(57) ABSTRACT

Braid-balls suitable for aneurysm occlusion and/or parent vessel occlusion/sacrifice (e.g., in treating neurovascular defects) are disclosed. Especially for aneurysm treatment, but also for either one of the aforementioned treatments, the form of the ball is very important. In particular, the density of the device is paramount in applications where braid itself is intended to moderate or stop blood flow—allowing thrombosis within a volume formed by the ball.

21 Claims, 2 Drawing Sheets

(56) References Cited

U.S. PATENT DOCUMENTS

| | | | |
|---|---|---|---|
| 4,655,771 | A | 4/1987 | Wallsten |
| 4,921,484 | A | 5/1990 | Hillstead |
| 4,998,539 | A | 3/1991 | Delsanti |
| 5,061,275 | A | 10/1991 | Wallsten et al. |
| 5,064,435 | A | 11/1991 | Porter |
| 5,104,404 | A | 4/1992 | Wolff |
| 5,122,136 | A | 6/1992 | Guglielmi et al. |
| 5,158,548 | A | 10/1992 | Lau et al. |
| 5,334,210 | A | 8/1994 | Gianturco |
| 5,378,239 | A | 1/1995 | Termin et al. |
| 5,405,379 | A | 4/1995 | Lane |
| 5,425,984 | A | 6/1995 | Kennedy et al. |
| 5,499,981 | A | 3/1996 | Kordis |
| 5,527,338 | A | 6/1996 | Purdy |
| 5,624,461 | A | 4/1997 | Mariant |
| 5,634,942 | A | 6/1997 | Chevillon et al. |
| 5,645,558 | A | 7/1997 | Horton |
| 5,690,671 | A | 11/1997 | McGurk et al. |
| 5,702,419 | A | 12/1997 | Berry et al. |
| 5,725,552 | A | 3/1998 | Kotula et al. |
| 5,728,906 | A | 3/1998 | Eguchi et al. |
| 5,733,294 | A | 3/1998 | Forber et al. |
| 5,741,333 | A | 4/1998 | Frid |
| 5,749,891 | A | 5/1998 | Ken et al. |
| 5,749,919 | A | 5/1998 | Blanc |
| 5,749,920 | A | 5/1998 | Quiachon et al. |
| 5,830,230 | A | 11/1998 | Berryman et al. |
| 5,846,261 | A | 12/1998 | Kotula et al. |
| 5,855,578 | A | 1/1999 | Guglielmi et al. |
| 5,879,366 | A | 3/1999 | Shaw et al. |
| 5,911,731 | A | 6/1999 | Pham et al. |
| 5,916,235 | A | 6/1999 | Guglielmi |
| 5,925,060 | A | 7/1999 | Forber |
| 5,928,228 | A | 7/1999 | Kordis et al. |
| 5,928,260 | A | 7/1999 | Chin et al. |
| 5,935,148 | A | 8/1999 | Villar et al. |
| 5,941,249 | A | 8/1999 | Maynard |
| 5,944,738 | A | 8/1999 | Amplatz et al. |
| 5,951,599 | A | 9/1999 | McCrory |
| 5,957,948 | A | 9/1999 | Mariant |
| 5,980,554 | A | 11/1999 | Lenker et al. |
| 6,010,517 | A | 1/2000 | Baccaro |
| 6,024,756 | A | 2/2000 | Huebsch et al. |
| 6,033,423 | A | 3/2000 | Ken et al. |
| 6,036,720 | A | 3/2000 | Abrams et al. |
| 6,059,813 | A | 5/2000 | Vrba et al. |
| 6,063,070 | A | 5/2000 | Eder |
| 6,063,104 | A | 5/2000 | Villar et al. |
| 6,086,577 | A | 7/2000 | Ken et al. |
| 6,093,199 | A | 7/2000 | Brown et al. |
| 6,096,034 | A | 8/2000 | Kupiecki et al. |
| 6,096,073 | A | 8/2000 | Webster et al. |
| 6,106,530 | A | 8/2000 | Harada |
| 6,123,715 | A | 9/2000 | Amplatz |
| 6,139,564 | A | 10/2000 | Teoh |
| 6,152,144 | A | 11/2000 | Lesh et al. |
| 6,168,592 | B1 | 1/2001 | Kupiecki et al. |
| 6,168,615 | B1 | 1/2001 | Ken et al. |
| 6,168,618 | B1 | 1/2001 | Frantzen |
| 6,168,622 | B1 | 1/2001 | Mazzocchi |
| 6,183,495 | B1 | 2/2001 | Lenker et al. |
| 6,190,402 | B1 | 2/2001 | Horton et al. |
| 6,193,708 | B1 | 2/2001 | Ken et al. |
| 6,221,086 | B1 | 4/2001 | Forber |
| 6,261,305 | B1 | 7/2001 | Marotta et al. |
| 6,280,412 | B1 | 8/2001 | Pederson, Jr. et al. |
| 6,306,141 | B1 | 10/2001 | Jervis |
| 6,309,367 | B1 | 10/2001 | Boock |
| 6,322,576 | B1 | 11/2001 | Wallace et al. |
| 6,325,820 | B1 | 12/2001 | Khosravi et al. |
| 6,331,184 | B1 | 12/2001 | Abrams |
| 6,332,576 | B1 | 12/2001 | Colley et al. |
| 6,342,068 | B1 | 1/2002 | Thompson |
| 6,344,041 | B1 | 2/2002 | Kupiecki et al. |
| 6,344,048 | B1 | 2/2002 | Chin et al. |
| 6,346,117 | B1 | 2/2002 | Greenhalgh |
| 6,350,270 | B1 | 2/2002 | Roue |
| 6,361,558 | B1 | 3/2002 | Hieshima et al. |
| 6,368,339 | B1 | 4/2002 | Amplatz |
| 6,375,668 | B1 | 4/2002 | Gifford et al. |
| 6,383,174 | B1 | 5/2002 | Eder |
| 6,391,037 | B1 * | 5/2002 | Greenhalgh ............... 606/151 |
| 6,409,750 | B1 | 6/2002 | Hyodoh et al. |
| 6,428,558 | B1 | 8/2002 | Jones et al. |
| 6,443,972 | B1 | 9/2002 | Bosma et al. |
| 6,447,531 | B1 | 9/2002 | Amplatz |
| 6,454,780 | B1 | 9/2002 | Wallace |
| 6,506,204 | B2 | 1/2003 | Mazzocchi |
| 6,511,468 | B1 | 1/2003 | Cragg et al. |
| 6,530,934 | B1 | 3/2003 | Jacobsen et al. |
| 6,544,278 | B1 | 4/2003 | Vrba et al. |
| 6,547,804 | B2 | 4/2003 | Porter et al. |
| 6,551,303 | B1 | 4/2003 | Van Tassel et al. |
| 6,569,179 | B2 | 5/2003 | Teoh et al. |
| 6,579,302 | B2 | 6/2003 | Duerig et al. |
| 6,579,303 | B2 | 6/2003 | Amplatz |
| 6,585,748 | B1 | 7/2003 | Jeffree |
| 6,585,756 | B1 | 7/2003 | Strecker |
| 6,589,256 | B2 | 7/2003 | Forber |
| 6,589,265 | B1 | 7/2003 | Palmer et al. |
| 6,592,605 | B2 | 7/2003 | Lenker et al. |
| 6,599,308 | B2 | 7/2003 | Amplatz |
| 6,605,102 | B1 | 8/2003 | Mazzocchi et al. |
| 6,605,111 | B2 | 8/2003 | Bose et al. |
| 6,613,074 | B1 | 9/2003 | Mitelberg et al. |
| 6,626,939 | B1 | 9/2003 | Burnside et al. |
| 6,635,068 | B1 * | 10/2003 | Dubrul et al. ............... 606/200 |
| 6,635,069 | B1 | 10/2003 | Teoh et al. |
| 6,652,555 | B1 | 11/2003 | VanTassel et al. |
| 6,652,556 | B1 | 11/2003 | VanTassel et al. |
| 6,666,882 | B1 | 12/2003 | Bose et al. |
| 6,666,883 | B1 | 12/2003 | Seguin et al. |
| 6,669,717 | B2 | 12/2003 | Marotta et al. |
| 6,669,721 | B1 | 12/2003 | Bose et al. |
| 6,676,696 | B1 | 1/2004 | Marotta et al. |
| 6,682,546 | B2 | 1/2004 | Amplatz |
| 6,689,150 | B1 | 2/2004 | VanTassel et al. |
| 6,689,486 | B2 | 2/2004 | Ho et al. |
| 6,695,876 | B1 | 2/2004 | Marotta et al. |
| 6,698,877 | B2 | 3/2004 | Urlaub et al. |
| 6,712,835 | B2 | 3/2004 | Mazzocchi et al. |
| 6,723,112 | B2 | 4/2004 | Ho et al. |
| 6,723,116 | B2 | 4/2004 | Taheri |
| 6,730,108 | B2 | 5/2004 | Van Tassel et al. |
| 6,746,468 | B1 | 6/2004 | Sepetka et al. |
| 6,746,890 | B2 | 6/2004 | Gupta et al. |
| 6,780,196 | B2 | 8/2004 | Chin et al. |
| 6,792,979 | B2 | 9/2004 | Konya et al. |
| 6,797,083 | B2 | 9/2004 | Peterson |
| 6,802,851 | B2 | 10/2004 | Jones et al. |
| RE38,653 | E | 11/2004 | Igaki et al. |
| 6,811,560 | B2 | 11/2004 | Jones et al. |
| 6,855,153 | B2 | 2/2005 | Saadat |
| 6,855,154 | B2 | 2/2005 | Abdel-Gawwad |
| RE38,711 | E | 3/2005 | Igaki et al. |
| 6,860,893 | B2 | 3/2005 | Wallace et al. |
| 6,936,055 | B1 | 8/2005 | Ken et al. |
| 6,949,103 | B2 | 9/2005 | Mazzocchi et al. |
| 6,949,113 | B2 | 9/2005 | Van Tassel et al. |
| 6,953,472 | B2 | 10/2005 | Palmer et al. |
| 6,989,019 | B2 | 1/2006 | Mazzocchi et al. |
| 6,994,092 | B2 | 2/2006 | Van der Burg et al. |
| 6,994,717 | B2 * | 2/2006 | Konya et al. ............... 606/200 |
| 7,011,671 | B2 | 3/2006 | Welch |
| 7,018,401 | B1 | 3/2006 | Hyodoh et al. |
| 7,029,487 | B2 | 4/2006 | Greene, Jr. et al. |
| 7,033,375 | B2 | 4/2006 | Mazzocchi et al. |
| 7,048,752 | B2 | 5/2006 | Mazzocchi et al. |
| 7,070,607 | B2 | 7/2006 | Murayama et al. |
| 7,070,609 | B2 | 7/2006 | West |
| 7,083,632 | B2 | 8/2006 | Avellanet et al. |
| 7,128,073 | B1 | 10/2006 | van der Burg et al. |
| 7,128,736 | B1 | 10/2006 | Abrams et al. |
| 7,169,177 | B2 | 1/2007 | Obara |

(56) References Cited

U.S. PATENT DOCUMENTS

| | | |
|---|---|---|
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,244,267 B2 | 7/2007 | Huter et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,597,704 B2 | 10/2009 | Frazier et al. |
| 7,608,088 B2 | 10/2009 | Jones et al. |
| 7,621,928 B2 | 11/2009 | Thramann et al. |
| 7,632,296 B2 | 12/2009 | Malewicz |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,016,869 B2 | 9/2011 | Nikolchev |
| 8,016,872 B2 | 9/2011 | Parker |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | van Tassel et al. |
| 8,261,648 B1 | 9/2012 | Marchand et al. |
| 8,430,012 B1 | 4/2013 | Marchand et al. |
| 8,454,681 B2 | 6/2013 | Holman et al. |
| 2001/0000797 A1 | 5/2001 | Mazzocchi |
| 2001/0012949 A1 | 8/2001 | Forber |
| 2002/0013618 A1 | 1/2002 | Marotta et al. |
| 2002/0042628 A1 | 4/2002 | Chin et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1* | 10/2003 | Palmer et al. ............... 606/200 |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0111112 A1 | 6/2004 | Hoffmann |
| 2004/0122467 A1 | 6/2004 | VanTassel et al. |
| 2004/0122468 A1 | 6/2004 | Yodfat et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215332 A1 | 10/2004 | Frid |
| 2004/0249408 A1 | 12/2004 | Murphy et al. |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0043759 A1 | 2/2005 | Chanduszko |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0228434 A1 | 10/2005 | Amplatz et al. |
| 2005/0267568 A1 | 12/2005 | Berez et al. |
| 2005/0288763 A1 | 12/2005 | Andreas et al. |
| 2006/0052816 A1 | 3/2006 | Bates et al. |
| 2006/0064151 A1 | 3/2006 | Guterman et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0206199 A1 | 9/2006 | Churchwell et al. |
| 2006/0206200 A1 | 9/2006 | Garcia et al. |
| 2006/0235464 A1 | 10/2006 | Avellanet et al. |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0282152 A1 | 12/2006 | Beyerlein et al. |
| 2006/0292206 A1 | 12/2006 | Kim et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0051705 A1 | 2/2008 | Von Oepen et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |

(56) References Cited

U.S. PATENT DOCUMENTS

| | | |
|---|---|---|
| 2008/0119886 A1 | 5/2008 | Greenhalgh et al. |
| 2008/0125806 A1 | 5/2008 | Mazzocchi et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0143851 A1 | 6/2009 | Paul, Jr. |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0264914 A1 | 10/2009 | Riina et al. |
| 2009/0275974 A1 | 11/2009 | Marchand et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030200 A1 | 2/2010 | Strauss et al. |
| 2010/0030220 A1 | 2/2010 | Truckai et al. |
| 2010/0042133 A1 | 2/2010 | Ramzipoor et al. |
| 2010/0069948 A1 | 3/2010 | Veznedaroglu et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0185271 A1 | 7/2010 | Zhang |
| 2010/0268260 A1 | 10/2010 | Riina et al. |
| 2010/0274276 A1 | 10/2010 | Chow et al. |
| 2011/0022149 A1 | 1/2011 | Cox et al. |
| 2011/0082493 A1 | 4/2011 | Samson et al. |
| 2011/0106234 A1 | 5/2011 | Grandt |
| 2011/0144669 A1 | 6/2011 | Becking et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Strivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0330341 A1 | 12/2012 | Becking et al. |
| 2013/0018451 A1 | 1/2013 | Grabowski et al. |
| 2013/0066357 A1 | 3/2013 | Aboytes et al. |
| 2013/0092013 A1 | 4/2013 | Thompson et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2014/0005713 A1 | 1/2014 | Bowman |

FOREIGN PATENT DOCUMENTS

| | | |
|---|---|---|
| DE | 1283434 B | 11/1968 |
| DE | 102008028308 | 4/2009 |
| DE | 102011011510 A1 | 8/2012 |
| EP | 775470 | 5/1997 |
| EP | 855170 A2 | 7/1998 |
| EP | 1621148 A1 | 2/2006 |
| EP | 1637176 | 3/2006 |
| EP | 1752112 | 2/2007 |
| EP | 1942972 | 7/2008 |
| EP | 1872742 B1 | 5/2009 |
| EP | 2157937 | 3/2010 |
| EP | 2279023 A2 | 2/2011 |
| EP | 2363075 | 9/2011 |
| EP | 2496299 A2 | 9/2012 |
| EP | 2675402 A2 | 12/2013 |
| FR | 2556210 B1 | 4/1988 |
| FR | 2890306 | 3/2007 |
| JP | 11-506686 | 6/1999 |
| JP | 2003520103 A | 7/2003 |
| JP | 2003-524434 A | 8/2003 |
| JP | 2004-049585 A | 2/2004 |
| JP | 2005-522266 A | 7/2005 |
| JP | 2006-506201 A | 2/2006 |
| JP | 2008-541832 A | 11/2008 |
| JP | 4673987 B2 | 4/2011 |
| WO | WO-88/00813 | 2/1988 |
| WO | WO-96/01591 | 1/1996 |
| WO | WO 97/26939 A1 | 7/1997 |
| WO | WO 99/03404 A1 | 1/1999 |
| WO | WO 99/05977 A1 | 2/1999 |
| WO | WO-99/08607 | 2/1999 |
| WO | WO-99/08743 | 2/1999 |
| WO | WO 99/62432 A1 | 12/1999 |
| WO | WO 01/93782 A1 | 12/2001 |
| WO | WO 02/00139 A1 | 1/2002 |
| WO | WO 02/071977 A2 | 9/2002 |
| WO | WO 2005/117718 A1 | 12/2005 |
| WO | WO 2006/026744 A1 | 3/2006 |
| WO | WO-2006/034166 A2 | 3/2006 |
| WO | WO 2006/091891 A2 | 8/2006 |
| WO | WO-2006/119422 A2 | 11/2006 |
| WO | WO-2007/047851 A2 | 4/2007 |
| WO | WO-2007/076480 A2 | 7/2007 |
| WO | WO 2007/121405 A2 | 10/2007 |
| WO | WO 2008/022327 A2 | 2/2008 |
| WO | WO 2008/151204 A1 | 12/2008 |
| WO | WO-2009/076515 | 6/2009 |
| WO | WO 2009/134337 A1 | 11/2009 |
| WO | WO-2009135166 A2 | 11/2009 |
| WO | WO-2010/028314 | 3/2010 |
| WO | WO 2010/030991 A1 | 3/2010 |
| WO | WO-2011/057277 A2 | 5/2011 |
| WO | WO-2011/130081 | 10/2011 |
| WO | WO-2011/153304 | 12/2011 |

OTHER PUBLICATIONS

PCT/US2009/041313 International Search Report, Jan. 14, 2010.
EP Serial No. 11173658.3 EESR, May 8, 2012.
EP Serial No. 11173659.1 EESR, May 8, 2012.
EP Serial No. 1189200.6 EESR, May 8, 2012.
EP Serial No. 12150960.8 ESR, Jun. 6, 2012.
EP Serial No. 12150959.0 ESR, Jun. 12, 2012.
EP Serial No. 1184201.9 EESR, Sep. 5, 2012.
Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.

(56) References Cited

OTHER PUBLICATIONS

U.S. Appl. No. 13/669,652, filed Nov. 6, 2012.
U.S. Appl. No. 13/629,678, filed Sep. 28, 2012.
U.S. Appl. No. 13/826,298, filed Mar. 14, 2013.
U.S. Appl. No. 13/795,556, filed Mar. 12, 2013.
U.S. Appl. No. 13/962,267, filed Aug. 8, 2013.

* cited by examiner

FILAMENTARY DEVICES FOR TREATMENT OF VASCULAR DEFECTS

CROSS REFERENCE TO RELATED APPLICATIONS

This filing is a continuation of U.S. patent application Ser. No. 12/427,620 filed Apr. 21, 2009 now U.S. Pat. No. 8,142,456 which claims the benefit of each of: U.S. Patent Application Ser. Nos. 61/046,594 and 61/046,670, both filed Apr. 21, 2008; U.S. Patent Application Ser. Nos. 61/083,957 and 61/083,961, both filed Jul. 28, 2008; and U.S. Patent Application Ser. No. 61/145,097, filed Jan. 15, 2009. Each of the foregoing applications is incorporated herein by reference in its entirety.

FIELD OF THE INVENTION

The present invention is directed to braid-balls suitable for aneurysm occlusion and/or parent vessel occlusion/sacrifice (e.g., in treating neurovascular defects).

BACKGROUND

Especially for aneurysm treatment, but also for either one of the aforementioned treatments, the form of the ball is very important. In particular, the density of the device is paramount in applications where braid itself is intended to moderate or stop blood flow—allowing thrombosis within a volume formed by the ball.

According to the present invention, braid-ball type implants are provided in braid of sufficient density is provided to moderate blood flow within the volume of the implant. Upon thrombosis, flow thereto is stopped. Alternatively, a blood-barrier covering can be applied to the filamentary structure to immediately stop blood flow into the vascular site, in which the implant volume is set.

In either case, to form thrombosis within the volume of the ball, the filaments of the braid matrix permit filling of the implant with blood when emplaced at a vascular treatment site. This blood then thromboses due to the flow-disruption effect(s).

Unlike Nitinol tube-cut cages that may be suitable for (or assist) in coil retention, the ball devices are adapted to work alone—or in combination with each other to effect a complete treatment. As such, high density braid/mesh is typically required. Namely, braid having at least about 48 ends, typically set at about 90 degrees or greater, in diameters from about 4 to about 8 mm may be employed. At larger diameters (e.g., about 6 to 12 or more), more wire ends (e.g., 64, 72 and upwards) may be employed in forming the balls.

Suitable braid for constructing the balls may be obtained from Secant Medical, Inc. Wire diameters may be in the range of about 0.001 to about 0.003 inches, depending on desired delivery profile (which is typically less than about 0.050 inches). The braid forming the balls may incorporate only one size wire, or may be formed with multiple sizes.

The wire is preferably superelastic NiTi alloy. The metal may be a binary alloy or a ternary alloy to provide additional radiopacity. Alternatively, radiopaque platinum fibers may be included in the braid, or the wire may comprise platinum or gold cord Nitinol DFT. Otherwise, wraps or bands (preferably Pt) used to secure the braid wire may serve as the sole radiopaque feature(s).

In any case, the construction approaches described herein enable producing these useful devices. Whether comprising braid alone, or incorporating some further blood-barrier covering (such as a thin urethane film as may be applied by Hantel, Inc. or others) the use of braid presents numerous challenges in managing the termination of multiple wires and in forming the desired structures.

Also included in the invention are detachable implant pushers that utilize a resistance wire heater to thermally sever a suture associated with the implant to effect release. As distinguished from known approaches where an implant is retained by a loop connected back to a delivery system pusher that is withdrawn with the devilry system, the present invention contemplates a leave-behind tether.

Further details, variations, modification and optional features of the invention may be appreciated by review of any of the incorporated patent applications. However, the priority date and subject matter included in the appended claims rely solely on the subject matter filed in U.S. Provisional Patent Application Nos. 61/046,670 and 61/046,594, the earliest patent applications (each filed Apr. 21, 2008) one which U.S. patent application Ser. No. 12/427,620 relies. Selected figures from the '670 and '594 application and all of text from the '594 application—all—incorporated by reference in the parent application hereto is reproduced herein.

DETAILED DESCRIPTION OF THE INVENTION

Implants

Referring to the figures, a filamentary implant 2 is formed out of braid to treat vascular sites. Interwoven filaments 4 form a braid matrix 6 that define a self-expandable occlusion device.

Figure 1:
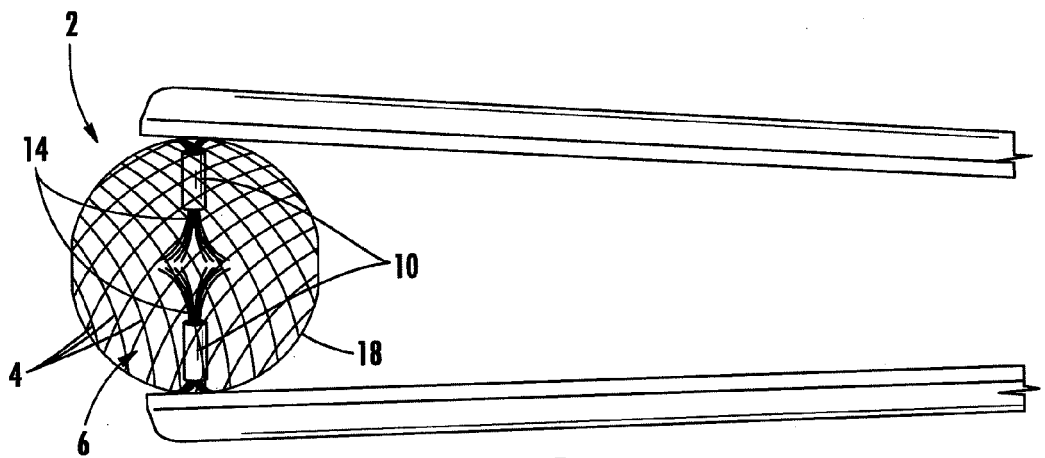
FIG. 1 is a photograph taken from U.S. Provisional Patent Appl. No. 61/046,670 (incorporated herein by reference) demonstrating actual reduction to practice of a single-layer braid ball device made according to the present invention.
Figure 2A:
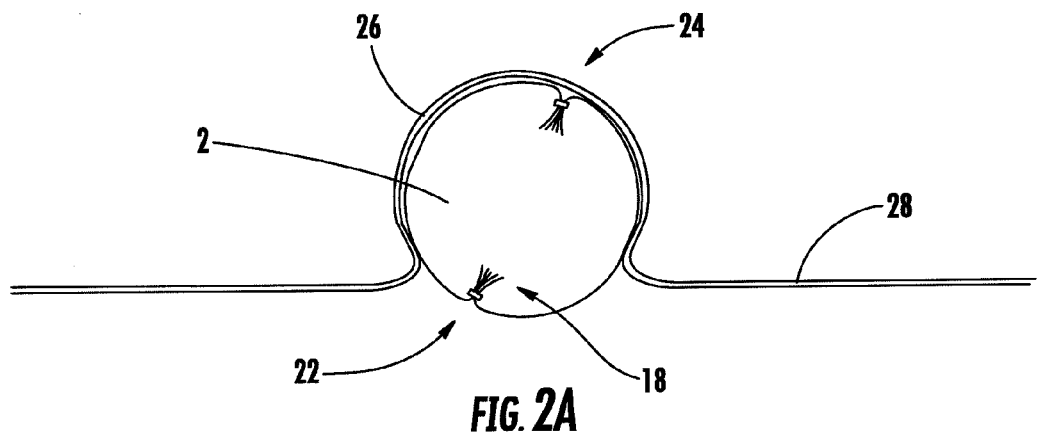
FIGS. 2A and 2B are side-sectional views of the braid ball in isolation and in use, respectively.
Figure 2B:
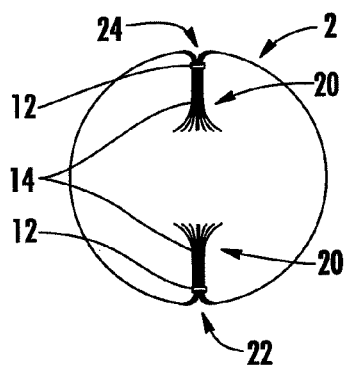

As single layer of the braid is provided in which ends of the braid are secured and managed to provide an atraumatic interface. Specifically, ties 10 (as illustrated in FIG. 1) or bands 12 (as illustrated in FIGS. 2A and 2B) secure filament the ends 14 of the braid from which the implant is constructed.

In the implant variation pictured, the expanded configuration defines an ovoid or roughly spherical shell 18 that is permeable to blood. The braid defining the proximal and distal ends of the implant turns or curves inward to a point where it is secured within the periphery of the shell.

The inversion of the braid provides recessed securement of the braid resulting in atraumatic ends of the implant. The braid filaments optionally extend beyond the securing/securement features in order to define wire filament "tufts" 20 that will further promote thrombosis of blood that enters the ball upon deployment within a patient's vasculature. However configured in regard to braid filament end securement and termination, inset ends of the braid (proximal and distal insets 22/24, respectively) are demonstrated when the implant is in an expanded state to fill an aneurysm 26 off of a vessel 28.

Delivery Systems

Figure 3:
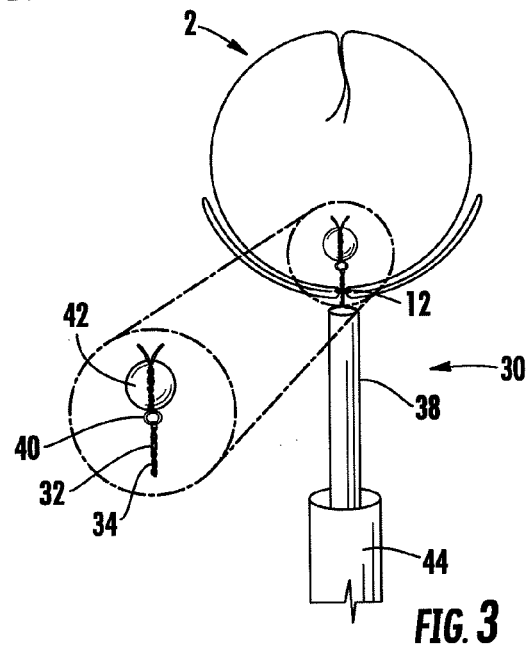
FIG. 3 illustrates a suture-melt resistance heater pusher for implant delivery.

FIG. 3 illustrates a detachable catheter/pusher 30, optionally, for use in the present invention. Generally, it includes a resistance wire bridge 32 across insulated conductors 34 (a typical construction). What is unique is that the conductor wires are twinned/twisted along a length of the delivery pusher shaft 38 as shown. This configuration alleviates bending bias/preference. Upon application of voltage, the tip thermally severs the polymer filament (e.g., suture 40) in contact therewith. At least the suture portion is received within the implant 2 (e.g., passing through a braid-securing band 12). The suture is retained in/with the implant upon actuation to release the implant by cutting through the suture with heat. A ball stop 42 that is tied to the suture retains the filament in/with the implant is also illustrated. Finally, pusher 30 is shown received within a typical microcatheter 44 for vascular access, after passage therethough. Note also, other advantageous delivery system are referenced and described in the incorporated patent application.

Methods of Manufacture

Included in the intention is a method of manufacture including tying-off or otherwise securing a second end of a braid within an interior volume of a ball where other approaches would be impracticable. The technique may be employed in creating the balls (be they spherical or ovaloid in cross-section, etc.) out of one continuous section of braid. In so doing, joints and other delivery profile-increasing features are avoided—as well as potential areas for failure. Accordingly, the subject implants are extremely robust and fully recoverable to their aneurysmal shape as is required when they are delivered through a catheter in low profile. Robust shape recovery is required in treatments targeting distal vasculature, especially the tortuous neurovasculature encountered in human brains.

Figure 4A:
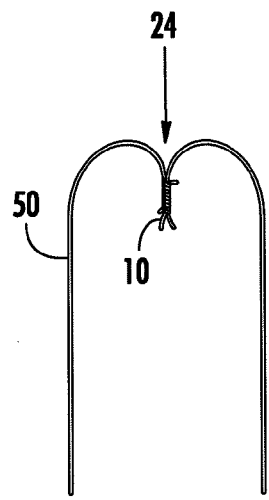
FIGS. 4A-4F illustrate a production path of one implant embodiment encompassed by the current invention.
Figure 4B:
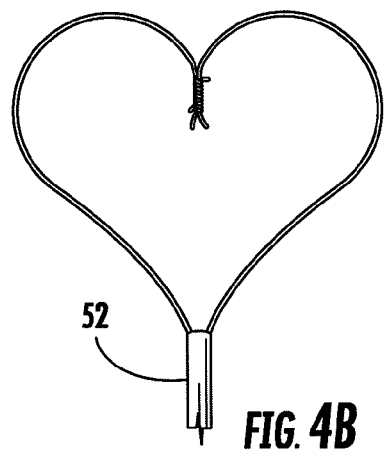
Figure 4C:
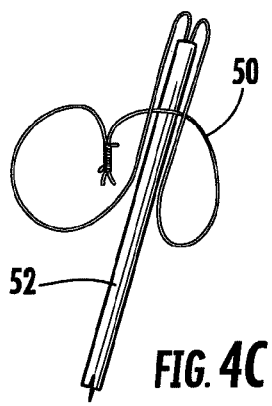
Figure 4D:
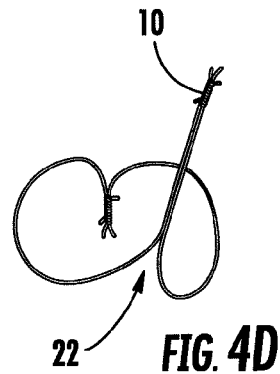
Figure 4E:
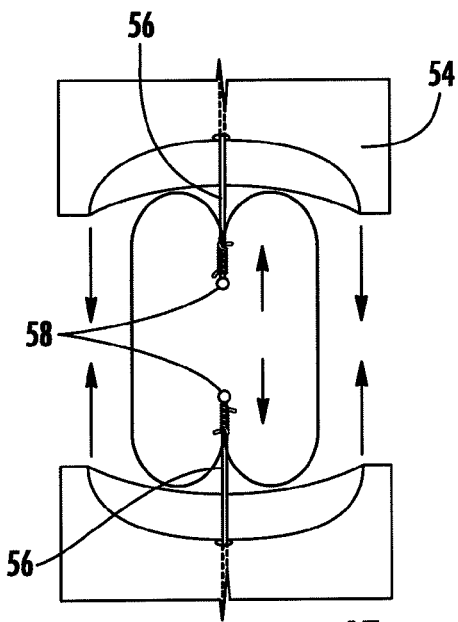
Figure 4F:
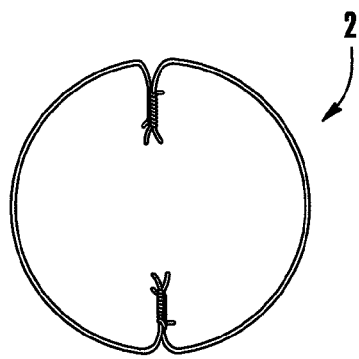

A detailed example of one process path for implant formation is illustrated in FIGS. 4A-4F. As shown in FIG. 4F an final implant 2 may begin as a section 50 of braided material. The tubular braid stock is secured. As shown, it is tied-off with a wire wrap 10. Such action develops an inset region 24 for the implant body. An opposite end of the braid is then captured in a transfer tube 52. The tube is passed through the volume of the implant and secured with a second tie 10 at the other side.

Additional refinement to the shape over that shown in FIG. 4E may be imparted within a shape-setting form 54. Mandrels 56 including stops 58 received through the securement features may be employed to force apposition of the ball to the shape of the form when pulled apart as indicated by arrows. After shape-setting in the form (as appropriate to the selected material—e.g., as in heat setting superelastic Nitinol) the mandrels are removed and the implant shaping is complete as shown in FIG. 4F. However, these additional forming steps are not necessary given that (in point of fact) the implant in FIG. 1 was produced without employing the same.

Methods of Use

Any one of the subject implants is delivered to a target site employing known percutaneous catheter access techniques. The implant may be secured to a pusher (e.g., pusher 30) used to advance it through the access catheter (e.g., microcatheter 44). Upon emplacement at the treatment site (e.g., cerebral aneurysm 26 as illustrated in FIG. 2A), the implant can be detached. With the exemplary system shown in FIG. 3, the suture 40 passing through the proximal end of the implant 2 is severed by melting it using a resistance heater. This retention/release fiber remains in and with the implant.

The invention claimed is:
1. A device for treatment of a patient's vasculature, comprising:
   a self-expanding resilient permeable shell having a proximal portion, a distal portion, a longitudinal axis and further comprising:
      a plurality of elongate resilient filaments with a woven structure secured relative to each other at the proximal and distal portions thereof, the filaments (i) radially converging to a first cross-section at each of the proximal and distal portions to form respective proximal and distal filament tufts, and (ii) radially diverging from the first cross-section to a second cross-section, larger than the first cross-section, such that free ends of the filaments flare outwardly within the shell for promoting thrombosis of blood;
      a radially constrained elongated state configured for delivery within a microcatheter with the thin woven filaments extending longitudinally from the proximal portion to the distal portion radially adjacent each other along a length of the filaments; and
      an expanded relaxed state with a globular and longitudinally shortened configuration relative to the radially constrained state with the woven filaments forming the self-expanding resilient permeable shell in a smooth path radially expanded from the longitudinal axis between the proximal portion and distal portion including a plurality of openings in the shell formed between the woven filaments, the largest of said openings being configured to allow blood flow through the openings at a velocity below a thrombotic threshold velocity.

2. The device of claim 1, wherein at least the shell distal portion includes a bend in a recessed configuration such that the distal filament tuft is disposed axially within a nominal contour of the permeable shell structure in the expanded state.

3. The device of claim 2, wherein the proximal portion of the shell further comprises a bend in a recessed configuration such that the proximal filament tuft is withdrawn axially within the nominal permeable shell.

4. The device of claim 1, wherein the filaments of the permeable shell are secured relative to each other in wraps or bands.

5. The device of claim 1, further comprising a distal hub secured to the distal filament tuft.

6. The device of claim 1, further comprising a proximal hub secured to the proximal filament tuft.

7. The device of claim 1, further comprising a band forming a cavity for a detachment tether.

8. The device of claim 7, further comprising a detachment tether secured through the cavity of the proximal hub.

9. The device of claim 1, wherein the filaments of the permeable shell have a transverse dimension of about 0.001 inch to about 0.003 inch.

10. The device of claim 1, wherein the permeable shell comprises at least about 72 filaments.

11. The device of claim 1, wherein the filaments of the permeable shell comprise a superelastic material.

12. The device of claim 11, wherein the superelastic material comprises a shape memory metal.

13. The device of claim 1, wherein the filaments of the permeable shell comprise a shape memory material that is heat set in a configuration of the relaxed expanded state.

14. The device of claim 13, wherein the shape memory metal comprises a NiTi alloy.

15. The device of claim 1, wherein the largest openings formed between adjacent filaments of a defect spanning portion of the permeable shell are about 0.017 inches to about 0.032 inches.

16. A delivery system for deployment of a device for treatment of a patient's vasculature, comprising:
- a microcatheter having an inner lumen extending a length thereof;
- a device for treatment of a patient's vasculature disposed within the inner lumen of the microcatheter and comprising a self-expanding resilient permeable shell of thin filaments, the permeable shell having a proximal portion, a distal portion, a longitudinal axis, a radially constrained elongated state, and an expanded state;
- wherein in the constrained state, the device is configured for delivery within a microcatheter with the thin woven filaments extending longitudinally from the proximal portion to the distal portion radially adjacent each other, and
- wherein in the expanded state, the filaments of the proximal and distal portions (i) radially converge to a first cross-section at each of the proximal and distal portions to form respective proximal and distal filament tufts, and (ii) radially diverge from the first cross-section to a second cross-section, larger than the first cross-section, such that free ends of the filaments flare outwardly within the shell for promoting thrombosis of blood, the device having, in the expanded state, a globular and axially shortened configuration relative to the constrained state with the woven filaments forming the self-expanding resilient permeable shell in a smooth path radially expanded from the longitudinal axis between the proximal portion and distal portion and a plurality of openings in the shell formed between the woven filaments, the permeable shell further having a portion when in the expanded relaxed state that is configured to span an opening of a patient's vascular defect; and
- an elongate delivery apparatus having a proximal end and a distal end releasably secured to a proximal hub of the device.

17. The system of claim 16, wherein at least the shell distal portion includes a bend in a recessed configuration such that the distal filament tuft is disposed axially within a nominal contour of the permeable shell structure in the expanded state.

18. The system of claim 17, wherein the proximal portion of the shell further comprises a bend in a recessed configuration such that the proximal filament tuft is disposed axially within the nominal contour of the permeable shell structure in the expanded state.

19. The system of claim 16, wherein the filaments of the permeable shell are secured relative to each other in wraps or bands.

20. The system of claim 16, wherein the device comprises a distal hub secured to the distal filament tuft.

21. The system of claim 16, wherein the device comprises a proximal hub secured to the proximal filament tuft.

* * * * *